(12) United States Patent
Perry

(10) Patent No.: US 8,021,701 B1
(45) Date of Patent: Sep. 20, 2011

(54) COMPOSITION TO RETARD THE ONSET OF SYMPTOMS OF ALZHEIMER'S DISEASE

(76) Inventor: Stephen C. Perry, Norwood, MA (US)

(*) Notice: Subject to any disclaimer, the term of this patent is extended or adjusted under 35 U.S.C. 154(b) by 1328 days.

(21) Appl. No.: 10/907,714

(22) Filed: Apr. 13, 2005

(51) Int. Cl.
*A61K 36/906* (2006.01)
*A61K 36/67* (2006.01)

(52) U.S. Cl. .................................... 424/756; 424/734

(58) Field of Classification Search .................. None
See application file for complete search history.

(56) References Cited

U.S. PATENT DOCUMENTS

| | | |
|---|---|---|
| 5,536,506 A | 7/1996 | Majeed et al. |
| 5,744,161 A | 4/1998 | Majeed et al. |
| 5,972,382 A | 10/1999 | Majeed et al. |
| 6,133,306 A | 10/2000 | Beal |
| 6,486,194 B2 | 11/2002 | Ducharme et al. |
| 6,572,899 B1 | 6/2003 | Gorsek |
| 6,646,013 B1 | 11/2003 | Barker et al. |
| 2001/0055630 A1* | 12/2001 | Castillo et al. ............... 424/769 |
| 2003/0113896 A1* | 6/2003 | Zinkowski et al. ........... 435/226 |
| 2003/0203057 A1* | 10/2003 | Okada et al. ................. 424/750 |
| 2004/0024048 A1* | 2/2004 | Wessel et al. ................ 514/440 |
| 2005/0058733 A1* | 3/2005 | Ochiai et al. ................. 424/756 |
| 2006/0116334 A1* | 6/2006 | Hendrix ........................ 514/27 |
| 2006/0160852 A1* | 7/2006 | Kimura et al. ................ 514/319 |
| 2006/0182828 A1* | 8/2006 | Colman ....................... 424/776 |

* cited by examiner

*Primary Examiner* — Christopher R Tate
*Assistant Examiner* — Deborah A. Davis
(74) *Attorney, Agent, or Firm* — Malin Haley Dimaggio Bowen & Lhota, P.A.

(57) ABSTRACT

A composition and a method for using the composition to delay the onset of the symptoms of Alzheimer's disease in humans, comprising curcumin, piperine, oleic acid, oleanolic acid, ursolic acid, galantamine, and huperzine A, among other compounds. Curcumin is an antioxidant, while galantamine and huperzine A inhibit the activity of acetylcholinesterase in the brain. Piperine and oleic acid increase the bioavailability and gastrointestinal absorption of curcumin, galantamine, huperzine A, and other nutrients.

12 Claims, 3 Drawing Sheets

FIG. 1

| Parameters | Curcumin alone 2 g/kg | Curcumin + Bioperine® 2g/kg + 20mg/kg |
|---|---|---|
| $C_{max}$ (mg/ml) | 1.35 ± 0.23 | 1.80 ± 0.16 |
| $T_{max}$ (h) | 0.83 ± 0.05 | 1.29 ± 0.23" |
| $t^1/_{2(a)}$ (h) | 0.31 ± 0.07 | 0.47 ± 0.03 |
| $t^1/_{2(el)}$ (h) | 1.70 ± 0.58 | 1.05 ± 0.18" |
| $AUC_{(0-tn)}$ (mg/h/ml) | 2.36 ± 0.28 | 3.64 ± 0.31 |
| $V_d$ (L/kg) | 1366.00 ± 248.70 | 782.90 ± 193.90 |
| Cl(L/h) | 713.00 ± 12.00 | 495.90 ± 37.08" |

"P < 0.02: Statistical significance by Student's "t" test.

$C_{max}$: Maximum serum concentration $T_{max}$: Time to reach maximal serum concentration $t^1/_{2(a)}$: Absorption half-life $t^1/_{2(el)}$: Elimination half-life AUC(0 - tn): Area under the concentration time curve $V_d$: Volume of distribution Cl: Total clearance

| Parameters | Curcumin alone 2 g | Curcumin+Bioperine® 2g+20mg |
|---|---|---|
| $C_{max}$ (mg/ml) | 0.006 ± 0.005 | 0.18 ± 0.03 |
| $T_{max}$ (h) | 1 | 0.69 ± 0.07 |
| $t^{1}/_{2(a)}$ (h) | - | 0.11 ± 0.02 |
| $t^{1}/_{2(el)}$ (h) | - | 0.41 ± 0.17 |
| $AUC_{(0-tn)}$ (mg/h/ml) | 0.004 | 0.08 ± 0.01 |
| $V_d$ (L/kg) | - | 202.60 ± 78.94 |
| Cl(L/h) | - | 7.33 ± 1.25 |
| F (Relative bioavailablility) | - | 2000% |

COMPOSITION TO RETARD THE ONSET OF SYMPTOMS OF ALZHEIMER'S DISEASE

FIELD OF THE INVENTION

This invention relates to a chemical composition and method for using said composition as a dietary supplement to increase the transfer of curcumin and other dietary substances and nutrients from the gastrointestinal tract into the bloodstream to retard the onset of symptoms of Alzheimer's disease in humans.

DESCRIPTION OF RELATED ART

Alzheimer's disease is a debilitating degenerative affliction of the nervous system, which will become increasingly common during the next three decades as the American population ages. In the baby-boomer generation in particular, has aged. Current estimates reveal that by 2035, when the average individual of the "baby boomer" generation is age 85, potentially 50% of Americans will have developed Alzheimer's disease. Alzheimer's Association website, http://search.alz.org/AboutAD/statistics.asp. By providing a treatment that can delay the onset of symptoms of Alzheimer's by as little as five years, at age 85, fifty percent of the United States cases of Alzheimer's could be eliminated. Id. Alzheimer's disease has a negative impact on an individual's memory and cognitive functions, ability to perform the simple activities of daily living, and causes behavioral problems among its sufferers with which families must learn to cope. Typically, Alzheimer's disease also reduces the lifespan of an individual by increasing one's risk of succumbing to secondary infections and illnesses. The disease is associated with the accumulation of β-amyloid plaques in the brain which leads to the eventual destruction of brain cells. The primary cause of Alzheimer's disease may be flaws in the metabolic processes governing production, accumulation, or disposal of the β-amyloid protein fragments. Therefore, treatments for Alzheimer's disease often have focused on dissolving β-amyloid or preventing the aggregation of the β-amyloid fragments into plaque formations.

Recent research has shown that people indigenous to the Indian subcontinent exhibit a much lower incidence of Alzheimer's disease than people living in the United States. Moreover, the research indicated that less than one percent of individuals in the examined population on the Indian subcontinent developed Alzheimer's and that the overall incidence rates of the disease in that location are among the lowest ever reported. V. Chandra et al., *Incidence of Alzheimer's disease in a rural community in India: the Indo-US study*, Neurology, 57(6): 985-989 (2001). Some researchers have attributed the low incidence of Alzheimer's disease in India to regional diets that are high in the curry spice, turmeric. Turmeric contains a substance, curcumin, which has demonstrated metabolic activity similar to non-steroidal anti-inflammatory drugs. Giselle P. Lim et al., *The Curry Spice Curcumin Reduces Oxidative Damage and Amyloid Pathology in an Alzheimer Transgenic Mouse*, Journal of Neuroscience, 21(21), 8370-8377 (2001).

Curcumin, a phenolic antioxidant phytochemical derived from the turmeric plant (*Curcuma longa*), is an effective antioxidant, antispasmodic, anti-inflammatory, anticoagulant, anticarcinogenic, and aids immunomodulatory activities and wound healing in the body. Id. at 8370. Curcumin exhibits an affinity for β-amyloid and both inhibits the aggregation of β-amyloid fragments into plaque formations as well as dissolves existing β-amyloid plaques. F. Yang et al., *Curcumin inhibits formation of Aβ oligomers and fibrils, binds plaques and reduces amyloid in vivo*, Journal of Biological Chemistry (2004).

As an antioxidant, curcumin removes harmful free radicals from the body, thereby protecting the human body, and particularly, the brain, by preventing lipid peroxidation. This antioxidant property of curcumin limits the formation and accumulation of β-amyloid plaques within the brain. Giselle P. Lim et al., *The Curry Spice Curcumin Reduces Oxidative Damage and Amyloid Pathology in an Alzheimer Transgenic Mouse*, Journal of Neuroscience, 21(21), at 8370 (2001). The non-steroidal anti-inflammatory activity of curcumin includes inhibiting cyclooxygenase 2, nuclear factor κB-mediated transcription of inflammatory cytokines, and the inhibition of inducible nitric oxide synthase. Id. at 8372. Research has shown that parenteral administering both low and high doses of curcumin reduces inflammation in the brain. Id. at 8373. Curcumin may also stimulate microglial phagocytosis of amyloid in the brain as well as destroy plaques that accumulate within the brain. Id. at 8375.

One disadvantage to the use of curcumin as an oral dietary supplement is that curcumin is poorly absorbed from inside the gastrointestinal tract into the human bloodstream. When ingested, curcumin normally remains in the gastrointestinal tract and uptake into the bloodstream is negligible. R. A. Sharma, *Preclinical pharmacokinetic study of dietary curcumin and its effects on biomarkers of cancer chemoprevention*, Clinical Cancer Research, Volume 6 (2000). Even with high dietary intake, curcumin is rapidly glucuronidated after ingestion, thereby resulting in low plasma levels of curcumin. F. Yang et al., *Curcumin inhibits formation of Aβ oligomers and fibrils, binds plaques and reduces amyloid in vivo*, Journal of Biological Chemistry, p. 22 (2004). Thus, current research indicates that orally administered curcumin, for the most part, is excreted in the feces without being absorbed and processed by the human body. To make available the beneficial effects of curcumin to Alzheimer's sufferers, the bioavailability of curcumin in the human body must be increased. Currently, clinical trials are being conducted at the University of California, Los Angeles, to examine the safety and tolerability of intravenous curcumin, and to determine the effect curcumin has as a treatment for patients suffering from mild to moderate Alzheimer's disease. John Ringman & Jenny Bardens, *A Phase II, Double-Blind, Placebo-Controlled Study of the Safety and Tolerability of Two Doses of Curcumin C3 Complex versus Placebo in Patients with Mild to Moderate Alzheimer's Disease*, National Institutes of Health, ClinicalTrials.gov (2003).

Piperine, a botanical extract from the fruits of *Piper nigrum* (black pepper) and *Piper longum*, has been determined to increase the bioavailability of curcumin in the body when both curcumin and piperine are taken together. Studies have shown that oral administration of 20.0 mg of piperine with 2.0 grams of curcumin increases the bioavailability of curcumin by 2,000%. U.S. Pat. No. 6,054,585, issued to Majeed et al., on Apr. 25, 2000, describes a process for making high-purity piperine from black pepper or long pepper for nutritional uses, however the '585 patent does not discuss the use of curcumin with piperine as a means for retarding the onset of Alzheimer's disease. U.S. Pat. Nos. 5,536,506, 5,744,161, and 5,972,382, issued to Majeed et al., on Jul. 16, 1996, Apr. 28, 1998, and Oct. 26, 1999, respectively, all describe the use of piper as a bioavailability enhancer for aiding and improving gastrointestinal absorption and systemic utilization of nutrients and nutritional supplements. The use of piperine to enhance the bioavailability of curcumin and other beneficial substances, which are not easily absorbed by the human gastrointestinal tract, is claimed by the '506, '161, and '382 patents, however, none of the three prior art patents mention the use of piperine for enhancing the bioavailability of curcumin to retard the onset of symptoms of Alzheimer's disease in humans as claimed by the applicant's current patent application.

Galantamine, a natural plant extract derived from the daffodil, snowdrop, and the spider lily, is an acetylcholinesterase inhibitor. Acetylcholinesterase is an enzyme that breaks down acetylcholine in the synaptic cleft between nerve cells. Acetylcholine is involved in memory and learning processes. Research has shown that the level of acetylcholine present in the nervous system of Alzheimer's patients is abnormally low. Galantamine increases the level of acetylcholine present in the brain by inhibiting the activity of acetylcholinesterase. In addition to being a useful therapeutic agent in the treatment of Alzheimer's disease, galantamine may also be useful for treating mild cognitive impairment, an age-related condition often diagnosed as a precursor condition and risk factor for developing Alzheimer's. Galantamine is also effective in treating Alzheimer's disease because it works to modulate nicotinic receptors on brain cells, which respond to acetylcholine, thereby preserving the number and functional integrity of nicotinic receptors in the brain. In Alzheimer's patients, the number and functional integrity of nicotinic receptors is diminished resulting in fewer receptors for acetylcholine. The benefits of treating Alzheimer's with galantamine are not affected by previous treatments using other acetylcholinesterase inhibitors. Thus, galantamine may work to effectively halt the progression of Alzheimer's disease and also allows a patient to regain some memory and cognitive functions as well as being able to perform some simple tasks of daily living. None of the three prior art patents mention the use of piperine for enhancing the bioavailability of galantamine to retard the onset of symptoms of Alzheimer's disease in humans as claimed by the applicant's current patent application.

Huperzine A, an alkaloid plant extract from the club moss *Huperzia serrata*, is a nootropic agent that also strongly inhibits the activity of acetylcholinesterase. As huperzine A inhibits the break down of acetylcholine by acetylcholinesterase, more acetylcholine becomes available to stimulate neurons. Huperzine A provides a long-lasting, potent means for inhibiting the enzymatic activity of acetylcholinesterase, thereby increasing the amount of acetylcholine present within the nervous system. The prior art does not describe the use of piperine for enhancing the bioavailability of huperzine A to retard the onset of symptoms of Alzheimer's disease in humans as claimed by the applicant's current patent application.

Oleic acid increases the absorptivity of the intestines so that food and nutrients can be fully absorbed into the body. In this way, oleic acid aids the body in digesting and processing substances that are difficult to digest. Bile (phosphatidylcholine) is the body's principle source of oleic acid in the small intestine, however only small amounts are produced. Oleanolic acid and ursolic acid share similar properties with oleic acid and also enhance the effects of curcumin in the body. The prior art, including the United States patents discussed above, does not describe the use of piperine for enhancing the bioavailability of oleic acid to retard the onset of symptoms of Alzheimer's disease in humans as claimed by the applicant's current patent application.

Pyritinol is a vitamin B6 derivative that improves glucose uptake within the brain, has antioxidant abilities, and enhances the immune system by increasing neutrophil activity. The Food and Drug Administration approved pyritinol for use to improve memory, concentration, and vigilance. Once again, the prior art does not describe the use of piperine for enhancing the bioavailability of pyritinol to retard the onset of symptoms of Alzheimer's disease in humans as claimed by the applicant's current patent application.

Vinpocetine is another drug that has shown memory-enhancing properties in humans. Vinpocetine is believed to enhance blood flow in the brain, safeguard brain cells against damage, and inhibit the activity of a substance known as phosphodiesterase, all of which would retard the chances of developing symptoms of Alzheimer's disease.

Vitamin B5, or pantothenic acid, is used by the human body along with choline to form acetylcholine. Thus, as important precursors to the formation of acetylcholine, which is often present in reduced levels in Alzheimer's patients, choline and vitamin B5 are necessary nutritional supplements for preventing the onset of symptoms associated with neurodegenerative disorders, such as Alzheimer's.

Gamma tocopherol, an analog of vitamin E, has been proven to act as a strong antioxidant useful in the prevention of the symptoms of Alzheimer's disease in humans. Sesame lignans, preferably in the form of sesamolin, enhances the bioavailability of gamma tocopherol at the cellular level, thereby increasing the effectiveness of gamma tocopherol in combating the effects of the symptoms of Alzheimer's disease.

U.S. Pat. No. 6,572,899, issued to Gorsek on Jun. 3, 2003, describes a composition of orally ingestible nutrients for treating memory loss, dementia, and Alzheimer's disease. The '899 patent does not describe the use of curcumin and piperine to delay the onset of symptoms of Alzheimer's disease as does the applicant's application.

U.S. Pat. No. 6,486,194, issued to Ducharme et al., on Nov. 26, 2002, describes the use of enzyme inhibitors to disrupt the activity of cyclooxygenase to treat neurodegenerative diseases, including Alzheimer's disease. Although the '194 patent claims the oral administration of an enzyme inhibitor, the particular enzyme inhibited in that patent is not acetylcholinesterase, nor does the '194 invention describe the use of curcumin or piperine to retard the symptoms of Alzheimer's disease.

U.S. Pat. No. 6,646,013, issued to Barker et al., on Nov. 11, 2003, describes a composition comprising multiple nutrients for reducing the risk of colorectal cancer in mammals. The '013 patent claims the use of curcumin as one of the cancer-preventing nutrients, however, the '013 does not describe the use of curcumin for preventing the onset of the symptoms of Alzheimer's disease in humans.

U.S. Pat. No. 6,133,306, issued to Beal on Oct. 17, 2000, describes a method of inhibiting neurodegenerative diseases, including Alzheimer's disease, by administering nitroindazole to a patient to inhibit a neuronal oxide synthase. The '306 patent does not describe the use of curcumin or piperine to delay the onset of the symptoms of Alzheimer's disease in humans.

OTHER PUBLICATIONS

K. Abascal & E. Yarnell, *Alzheimer's disease: part 1-biology and botanicals*, Alternative & Complementary Therapies, 10(1), 18-21 (2004).

K. Abascal & E. Yarnell, *Alzheimer's disease: part 2-a botanical treatment plan*, Alternative & Complementary Therapies, 10(2), 67-72 (2004).

H. P. T. Ammon & M. A. Wahl, *Pharmacology of Curcuma longa*, Planta Medica, vol. 57, 1-7 (1997).

R. B. Arora et al., *Anti-inflammatory studies on Curcuma longa (Turmeric)*, Indian Journal of Medical Research, 59(8), 1289-1295 (1971).

Atal et al., Biochemical Basis of Enhanced Drug Bioavailability by Piperine: Evidence that Piperine is a Potent Inhibitor of Drug Metabolism, Journal of Pharmacology & Experimental Therapeutics, 232(1), 258-262 (1985).

Atal et al., Scientific Evidence on the Role of Ayurvedic Herbals on Bioavailability of Drugs, Journal of Ethnopharmacology, vol. 4, 229-232 (1981).

D. L. Bai et al., Huperzine A, a potential therapeutic agent for treatment of Alzheimer's disease, Current Medicinal Chemistry, 7(3), 355-374 (2000).

Bano et al., Effect of piperine on bioavailability and pharmacokinetics of propranolol and theophylline in healthy volunteers, European Journal of Clinical Pharmacology, 41:615-617 (1991).

Bano et al., The Effect of Piperine on Pharmacokinetics of Phenytoin in Healthy Volunteers, Planta Medica, vol. 17, 568-569 (1987).

D. Bereczki & I. Fekete, *A systematic review of vinpocetine therapy in acute ischaemic stroke*, European Journal of Clinical Pharmacology, 55:349-352 (1999).

*Bioperine®-Nature's Bioavailability Enhancing Thermonutrient*, Executive Summary, Sabinsa Corporation, Piscataway, N.J. (1996).

J. Blasiak et al., *Curcumin damages DNA in human gastric mucosa cells and lymphocytes*, Journal of Environmental Pathology, Toxicology and Oncology, 18(4), 271-276 (1999).

F. Bonté et al., Protective effect of curcuminoids on epidermal skin cells under free oxygen radical stress, Planta Medica, vol. 63, 265-266 (1997).

Chem. Abstracts, 118: 6637, Johri et al., *An Ayurvedic formulation 'Trikatu and its Constituents'*, Journal of Ethnopharmacology, 37(2), 85-91 (1992).

Chem. Abstracts, 110: 6454, Wood et al., Overseas Dev. Nat. Resource Inst., 3(2), 55-64 (1988).

D. Choudhary et al., *Modulation of radioresponse of glyoxalase system by curcumin*, Journal of Ethnopharmacology, vol. 64, 1-7 (1999).

Dahanukar et al., Influence of Trikatu Powder on Rifampicin Bioavailability, Indian Drugs, July 1983, 402-404.

DeKosky, Presentation to the Senate Appropriations Committee; Labor, Health and Human Services, Education, and Related Agencies Subcommittee (2001).

S. D. Deodhar et al., *Preliminary study on antirheumatic activity of curcumin (diferoyl methane)*, Indian Journal of Medical Research, vol. 71, 632-634 (1980).

S. S. Deshpande & G. B. Maru, Effects of curcumin on the formation of benzo[a]pyrene derived DNA adducts in vitro, Cancer Letters, vol. 96, 71-80 (1995).

U. R. Deshpande et al., Protective effect of turmeric (*Curcuma longa* L.) extract on carbon tetrachloride-induced liver damage in rats, Indian Journal of Experimental Biology, vol. 36, 573-577 (1998).

M. S. Ebadi, Pharmacodynamic basis of herbal medicine, CRC Press (2002).

T. Erkinjuntti et al., Efficacy of galantamine in probable vascular dementia and Alzheimer's disease combined with cerebrovascular disease: a randomised trial, Lancet, vol. 359, 1283-1290 (2002).

E. Ernst, Herbal medications for common ailments in the elderly, Drugs and Aging, 15(6), 423-428 (1999).

H. J. Gertz & M. Kiefer, *Review about Ginkgo biloba special extract EGb 761 (Ginkgo)*, Current Pharmaceutical Design, 10(3), 261-264 (2004).

P. E. Gold et al., *The lowdown on Ginkgo biloba*, Scientific American, 288(4), 86-91 (2003).

M. Grundman & P. Delaney, *Antioxidant strategies for Alzheimer's disease*, Proceedings of the Nutrition Society, 61(2), 191-202 (2002).

M. J. Howes et al., Plants with traditional uses and activities, relevant to the management of Alzheimer's disease and other cognitive disorders, Phytotherapy Research, 17(1), 1-18 (2003).

S. Kanowski & R. Hoerr, Ginkgo biloba extract EGb 761 in dementia: intent-to-treat analyses of a 24-week, multi-center, double-blind, placebo-controlled, randomized trial, Pharmacopsychiatry, 36(6), 297-303 (2003).

Kawada et al., *Rapid Communication*, Proceedings of the Society for Experimental Biology and Medicine, 188, 229-233 (1988).

B. Kiss B & E. Karpati, Mechanism of action of vinpocetine [in Hungarian; English abstract], Acta Pharm Hung, 66:213-214 (1996).

D. S. Knopman, Part VI: primary drug therapies for Alzheimer's disease-noncholinominetic drugs-alternative medicines, Disease-a-Month: DM, 46(11), 745-760 (2000).

S. Lalitha & R. Selvam, Prevention of H2Os-induced red blood cell lipid peroxidation by aqueous extracted turmeric, Asia Pacific Journal of Clin. Nutr., 8(2), 113-114 (1999).

P. L. Le Bars et al., Influence of the severity of cognitive impairment on the effect of the Ginkgo biloba extract EGb 761 in Alzheimer's disease, Neuropsychobiology, 45(1), 19-26 (2002).

M. Majeed et al., *Curcuminoids*, NutriScience Publishers (1995).

J. E. Mintzer & P. Kershaw, The efficacy of galantamine in the treatment of Alzheimer's disease: comparison of patients previously treated with acetylcholinesterase inhibitors to patients with no prior exposure, International Journal of Geriatric Psychiatry, vol. 18, 292-297 (2003).

M. Miyazaki, The effect of a cerebral vasodilator, vinpocetine, on cerebral vascular resistance evaluated by the Doppler ultrasonic technique in patients with cerebrovascular diseases, Angiology, 46:53-58 (1995).

C. Nirmala et al., Curcumin treatment modulates collagen metabolism in isoproterenol induced myocardial necrosis in rats, Molecular and Cellular Biochemistry, vol. 197, 31-37 (1999).

B. S. Oken et al., The efficacy of Ginkgo biloba on cognitive function in Alzheimer disease, Archives of Neurology, 55(11), 1409-1415 (1998).

J. Olin & L. Schneider, *Galantamine for Alzheimer's disease (Cochrane review)*, In The Cochrane Library, Issue 2 (2001).

B. R. Ott & N. J. Owens, *Complementary and alternative medicines for Alzheimer's disease*, Journal of Geriatric Psychiatry and Neurology, 11(4), 163-173 (1998).

PDR FOR HERBAL MEDICINES, Medical Economics Company, (2000).

E. J. Park et al., Protective effect of curcumin in rat liver injury induced by carbon tetrachloride, Journal of Pharm. Pharmacol., vol. 52, 437-440 (2000).

E. K. Perry et al., *Medicinal plants and Alzheimer's disease: from ethnobotany to phytotherapy*, Journal of Pharmacy and Pharmacology, 51(5), 527-534 (1999).

D. Pratico & N. Delanty, Oxidative injury in diseases of the central nervous system: focus on Alzheimer's disease, American Journal of Medicine, 109(7), 577-585 (2000).

V. Rajakrishnan et al., Neuroprotective role of curcumin from *Curcuma longa* on ethanol-induced brain damage, Phytotherapy Research, vol. 13, 571-574 (1999).

A. Ramirez-Bosca et al., Antioxidant curcuma extracts decrease the blood peroxide levels of human subjects, Age, vol. 18, 167-169 (1995).

R. S. Ramsewak et al., Cytotoxicity, antioxidant, and anti-inflammatory activities of Curcumins I-III from Curcuma longa, Phytomedicine, 7(4), 303-308 (2000).

N. S. Rao & M. N. A. Rao, *Free radical scavenging activity of curcuminoids*, Arzneim.-Forsch./Drug Res., 46(2), 169-171 (1996).

N. S. Rao & M. N. A. Rao, *Nitric oxide scavenging by curcuminoids*, Journal of Pharm. Pharmacol., vol. 49, 105-107 (1997).

M. A. Raskind et al., Galantamine in Alzheimer's disease: a 6-month, randomized, placebo-controlled trial with a 6-month extension, Neurology, vol. 54, 2261-2268 (2000).

R. R. Satoskar et al., *Evaluation of anti-inflammatory property of curcumin (diferoyl methane) in patients with post-operative inflammation*, International Journal of Clinical Pharmacology, Therapy and Toxicology, 24(12), 651-654 (1986).

G. Shoba et al., Influence of piperine on the pharmacokinetics of curcumin in animals and human volunteers, Planta Medica, 64(4), 353-356 (1998).

A. A. Skolnick, *Old Chinese herbal medicine used for fever yields possible new Alzheimer disease therapy*, JAMA: Journal of the American Medical Association, 277(10), 776 (1997).

J. M. Snow, *Herbal Monograph: Curcuma longa L. (Zingiberaceae)*, The Protocol Journal of Botanical Medicine, Autumn issue, 43-46 (1995).

P. R. Solomon et al., *Ginkgo for memory enhancement: a randomized controlled trial*, JAMA: Journal of the American Medical Association, 288(7), 835-840 (2002).

R. C. Srimal, Turmeric: a brief review of its medicinal properties, Fitoterapia, 68(6), 483-493 (1997).

R. W. Stackman et al., Prevention of age-related spatial memory deficits in a transgenic mouse model of Alzheimer's disease by chronic Ginkgo biloba treatment, Experimental Neurology, 184(1), 510-520 (2003).

SUBBARAM, Specification for Indian Patent No. 1232/DEL/89.

M. Subramanian et al., Diminution of singlet oxygen-induced DNA damage by curcumin and related antioxidants, Mutation Research, vol. 311, 249-255 (1994).

P. N. Tariot et al., A 5-month, randomized, placebo-controlled trial of galantamine in Alzheimer's disease, Neurology, vol. 54, 2269-2276 (2000).

M. van Dongen et al., Ginkgo for elderly people with dementia and age-associated memory impairment: a randomized clinical trial, Journal of Clinical Epidemiology, 56(4), 367-376 (2003).

G. K. Wilcock et al., Efficacy and safety of galantamine in patients with mild to moderate Alzheimer's disease: multicentre randomised controlled trial, BMJ, 321(7274), 1445-1449 (2000).

A. Zangara, The psychopharmacology of huperzine A: an alkaloid with cognitive enhancing and neuroprotective properties of interest in the treatment of Alzheimer's disease, Pharmacology, Biochemistry and Behavior, 75(3), 675-686 (2003).

Zutshi et al., Influence of Piperine on Rifampicin Blood Levels In Patients Of Pulmonary Tuberculosis, JAP1, 33(3), 223-224 (1985).

SUMMARY OF THE INVENTION

The applicant's invention is for a composition and method for using said composition as a dietary supplement to retard the onset of the symptoms of Alzheimer's disease in humans. The composition comprises a mixture of curcumin, piperine, oleic acid, oleanolic acid, ursolic acid, galantamine, huperzine A, choline, and vitamin B5. The composition may also include gamma tocopherol, sesame lignans preferably in the form of sesamolin, vinpocetine, and/or pyritinol. Said composition can be produced as a dietary supplement for human ingestion in any orally administrable form including, but not limited to, a caplet, capsule, tablet, jelly, serum, or drink. Piperine, a botanical pepper extract derived from the fruits of *Piper nigrum* (black pepper) and *Piper longum* (long pepper), increases the bioavailability of curcumin in humans by increasing the absorption of curcumin from the gastrointestinal tract into the bloodstream.

The composition contains each ingredient in the following ranges: 2.0-100.0 mg curcumin, 2.0-20.0 mg piperine, 20.0-100.0 mg oleic acid, 20.0-100.0 mg oleanolic acid, 20.0-100.0 mg ursolic acid, 5.0-200.0 mg galantamine, 25.0-250.0 µg huperzine A, 5.0-150.0 mg choline, and 20.0-200.00 mg vitamin B5. Gamma tocopherol, an optional ingredient, is included in the range of 150.0-250.0 mg, and sesamolin, another optional ingredient, is included in the composition at 10.0-40.0 mg. If desired, vinpocetine, which is an optional ingredient of the mixture, can be included at 5.0-150.0 mg, and pyritinol, also an optional ingredient in the composition, may be included in an amount ranging from 20.0-200.0 mg.

An object of this invention is to provide a composition, ingestible as a dietary supplement, for delaying the onset and progression of symptoms of Alzheimer's disease in humans.

Another object of this invention is to provide a composition for retarding the onset and progression of symptoms of Alzheimer's disease in humans that contains curcumin.

Still another object of this invention is to increase the bioavailability of curcumin and other nutrients ingested by including piperine in a composition for retarding the onset and progression of symptoms of Alzheimer's disease in humans.

Yet another object of this invention is to provide an additional source of choline to the human body for use in forming acetylcholine, thereby enhancing the functionality of nerves in the brain, which use acetylcholine for neural transmissions.

A further object of this invention is to provide a composition for retarding the onset and progression of symptoms of Alzheimer's disease in humans that will prevent the aggregation of and dissolve β-amyloid protein fragments in the brain.

Another object of this invention is to provide a method for retarding the onset and progression of the symptoms of Alzheimer's disease in humans using the composition described herein as an ingestible dietary supplement taken orally in a beneficial regimen to be clinically determined.

In accordance with these and other objects which will become apparent hereinafter, the instant invention will now be described with particular reference to the accompanying drawings.

BRIEF DESCRIPTION OF THE DRAWINGS

FIG. 1 shows a table of the pharmacokinetic parameters (mean±SEM) of oral curcumin 2.0 g/kg alone and in combination with a source of piperine, Bioperine® 20 mg/kg, in rats (n=6).

DETAILED DESCRIPTION

The present invention relates to a composition for use as an orally-administered dietary supplement to delay the onset and symptoms of Alzheimer's disease in humans. Said composition comprises a mixture of curcumin for delaying the onset and progress of Alzheimer's disease symptomology in humans and piperine, a botanical pepper extract, for increasing the bioavailability of curcumin in the bloodstream when said curcumin is orally administered to a patient. Preferably, the composition also includes oleic acid, oleanolic acid, ursolic acid, galantamine, huperzine A, choline, and vitamin B5. The composition may further include vinpocetine, pyritinol, gamma tocopherol, and/or sesame lignans, preferably in the form of sesamolin. Said composition can be produced as a dietary supplement for human ingestion in any orally administrable form including, but not limited to, a caplet, capsule, tablet, jelly, serum, or drink. Piperine, a botanical pepper extract, is derived from the fruits of plants in the Piperaceae family, and preferably from the fruits of *Piper nigrum* and *Piper longum*. Most preferably, the piperine used in the composition is derived from the fruits of *Piper nigrum*, i.e. black pepper. The purpose of including piperine is to increase the bioavailability of curcumin and other substances in humans by increasing the absorption of curcumin and other nutrients from the gastrointestinal tract.

EXAMPLE 1

Bioavailability Studies

Curcumin and Piperine

Figures 2, 3:
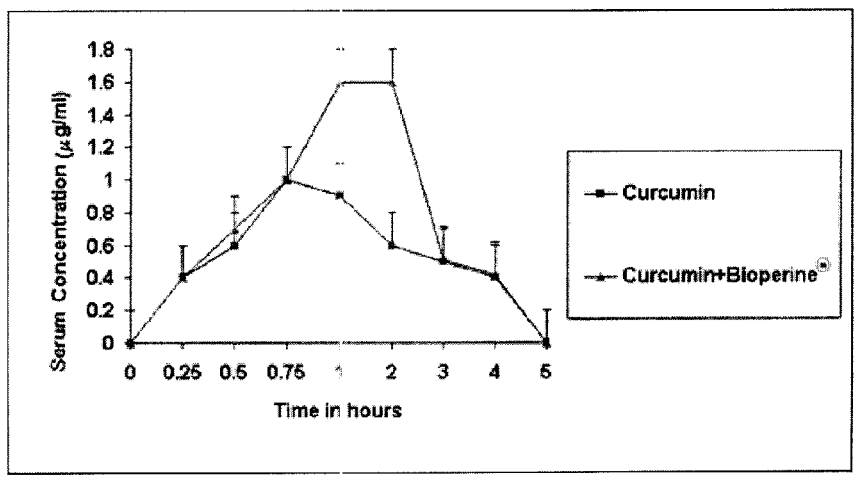
FIG. 2 shows a graphical representation of the effect of piperine (Bioperine®) on serum concentrations of curcumin in rats.
FIG. 3 shows a table of the pharmacokinetic parameters (mean±SEM) of oral curcumin 2.0 g alone and in combination with a source of piperine, Bioperine® 20 mg, in normal healthy volunteers (n=8).
Figure 4:
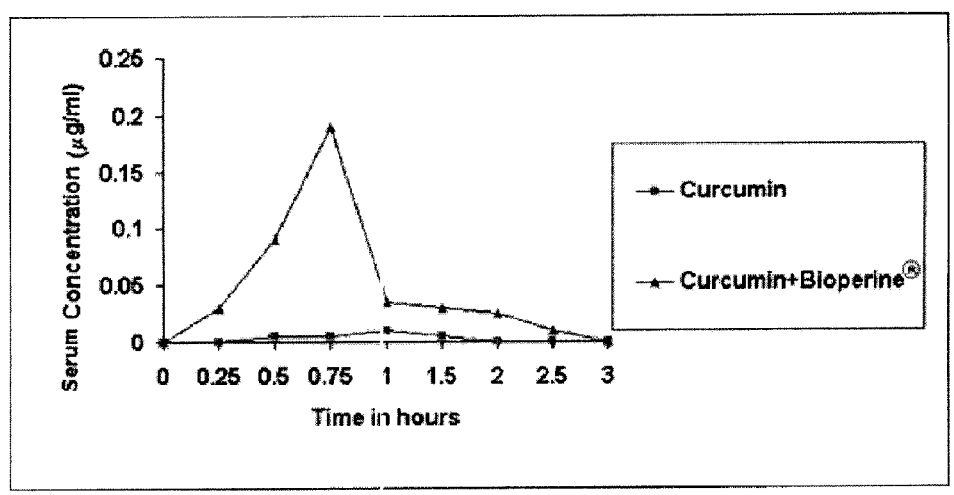
FIG. 4 shows a graphical representation of the effect of piperine (Bioperine®) on serum concentrations in normal healthy human volunteers.

In this study, the bioavailability of curcumin was evaluated, with said curcumin being orally administered to animals, and subsequently, to normal healthy human volunteers along with a source of piperine (Bioperine® was the source of piperine used in this study). When taken orally only traces of curcumin appeared in the blood, whereas most of the oral dose was excreted though the feces. In both the preclinical studies performed on rats and in the clinical studies using normal healthy volunteers, piperine enhanced the bioavailability of curcumin as demonstrated in FIGS. 1 through 4.

EXAMPLE 2

Proposed Clinical Trial of the Effectiveness of the Composition in Treating the Symptoms of Alzheimer's Disease To test the effectiveness of the composition in delaying the onset of the symptoms of Alzheimer's disease, a dietary supplement preparation is administered orally to patients who have manifested the symptoms of an early stage of Alzheimer's disease, as diagnosed by their physician and confirmed by an independent board-certified neurologist. Two weeks before the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated on Day 0, at 6 weeks, and at 3 months during the clinical trial. The tests are performed by neuropsychologists who are not aware of the patients' treatment regimen.

In this double blind study, patients are randomly assigned to the test composition or placebo at the beginning of the study. The test composition and placebo are administered orally one or two times per day. The test patients are evaluated for a period of five years to determine the effectiveness of treatment using the composition as compared to the control group individuals given a placebo. Scores are statistically compared between the test composition and the placebo for each of the three observational periods. Without treatment, the natural course of Alzheimer's disease results in significant deterioration of a patient's test scores during the course of the clinical trial. A patient treated with the composition is considered improved if the patient's scores remain the same or improve during the course of the clinical trial.

The preferred composition contains each ingredient in the following ranges and preferred ranges: Curcumin is included at 2.0-100.0 mg, and preferably at 10.0-40.0 mg. Piperine is included at 2.0-20.0 mg, and preferably at 5.0-10.0 mg. Oleic acid is included in the composition between a range of 20.0-100.0 mg, and preferably in the amount of 40 mg. Oleanolic acid is included in the composition between a range of 20.0-100.0 mg, and preferably in the amount of 40 mg. Ursolic acid is included in the composition between a range of 20.0-100.0 mg, and preferably in the amount of 40 mg. Galantamine is included in an amount ranging from 5.0-200.0 mg, and preferably at 16.0-24.0 mg. Huperzine A is included in the mixture at 25.0-250.0 µg, and preferably at 50.0-100.0 µg.

Choline is included in the composition at 5.0-150.0 mg, and preferably at 20.0-50.0 mg. Vitamin B5, or pantothenic acid, is included at 20.0-200.00 mg, and preferably at 50.0-100.00 mg. Gamma tocopherol, an optional ingredient, is included in the range of 150.0-250.0 mg, and preferably at 200.0 mg. Sesame lignans, preferably in the form of sesamolin and also an optional ingredient, is included in the composition at 10.0-40.0 mg, and preferably at 20.0 mg. If desired, vinpocetine, which is an optional ingredient of the mixture, is included at 5.0-150.0 mg, and preferably at 20.0-50.0 mg. Pyritinol, also an optional ingredient in the composition, may be included in an amount ranging from 20.0-200.0 mg, and preferably at 100.0 mg.

This invention also relates to a method for delaying the onset of symptoms of Alzheimer's disease in humans using the above-described composition as an ingestible dietary supplement. Preferably, the dietary supplement containing the composition is taken once or twice daily by a user. In this method, said composition may be produced and ingested in any orally administrable form including, but not limited to, a caplet, capsule, tablet, jelly, serum, or drink. The composition and method may also be used to delay the onset of symptoms of other neurodegenerative diseases, similar to Alzheimer's disease, that affect aging humans, including, but not limited to, Parkinson's disease.

The instant invention has been shown and described herein in what is considered to be the most practical and preferred embodiment. The applicant recognizes, however, that departures may be made therefrom within the scope of the invention and that obvious modifications will occur to a person skilled in the art.

What is claimed is:

1. A composition used as a dietary supplement for orally administering to human patients who have manifested the symptoms of an early stage of Alzheimer's disease as diagnosed by their physician, wherein the composition comprises effective amounts of:
   curcumin;
   piperine;
   oleic acid;
   oleanolic acid;
   galantamine;
   huperzine A;
   choline; and
   vitamin B5.

2. A composition used as a dietary supplement for orally administering to a human patients who have manifested the symptoms of an early stage of Alzheimer's disease as diagnosed by their physician comprising a mixture of:
   2.0-100.0 mg curcumin;
   2.0-20.0 mg piperine;
   20.0-100.0 mg oleic acid;
   20.0-100 mg oleanolic acid;
   20.0-100.0 mg ursolic acid;
   5.0-200.0 mg galantamine;
   25.0-250.0 ug huperzine A;
   5.0-150.0 mg choline; and
   20.0-200.0 mg vitamin B5.

3. The composition according to claim 2, wherein the piperine is in the form of a botanical pepper extract obtained from the fruits of plants in the Piperaceae family, including but not limited to, fruits of plants in the Piperaceae family, including but not limited to, fruits of *Piper nigrum* and *Piper longum*.

4. The composition according to claim 3, wherein the piperine is obtained from the fruits of *Piper nigrum*.

5. The composition according to claim 2, wherein said composition is produced as a dietary supplement for human ingestion in any orally administerable form including, but not limited to, a caplet capsule, tablet, jelly, serum, or drink.

6. The composition according to claim 2, wherein said composition optionally also comprises vinpocetine, gamma tocopherol, and/or sesame lignans, wherein the sesame lignans are preferably in the form of sesamolin, and/or pyritinol.

7. The composition according to claim 2, wherein said composition further comprises the following ranges of the ingredients:
   150.0-250.0 mg gamma tocopherol;
   10.0-40.0 mg sesame lignans, preferably in the form of sesamolin;
   5.0-150.0 mg vinpocetine; and
   20.0-200.0 mg pyritinol.

8. The composition according to claim 2, wherein said composition preferably contains the following preferred ranges of ingredients:
   10.0-40.0 mg curcumin;
   5.0-10.0 mg piperine;
   40.0 mg oleic acid
   40.0 mg oleanolic acid;
   40.0 mg ursolic acid;
   16.0-24.0 mg galantamine;
   50.0-100 ug huperzine A;
   20.0-50.0 mg choline; and
   50.0-100.00 mg vitamin B5.

9. The composition according to claim 8, wherein said composition further comprises the following preferred ranges of the ingredients listed below:
   200.0 mg gamma tocopherol;
   20.0 mg sesame lignans, preferably in the form of sesamolin;
   20.0-50.0 mg vinpocetine; and
   100.0 mg pyritinol.

10. A method for treating symptoms of Alzheimer's disease in a human, comprising administering to a subject in need thereof a dietary supplement composition comprising effective amounts of:
    curcumin;
    piperine;
    oleic acid;
    oleanolic acid;
    galantamine;
    huperzine A;
    choline; and
    vitamin B5.

11. The method of claim 10, wherein said composition also optionally comprises vinpocetine, gamma tocopherol, and/or sesame lignans, wherein the sesame lignans are preferably in the form of sesamolin, and/or pyritinol.

12. The method of claim 10, wherein said composition can be produced and ingested in any orally administrable form including, but not limited to, a caplet, capsule, tablet, jelly, serum, or drink.

* * * * *